United States Patent [19]

Katz

[11] Patent Number: 5,246,021

[45] Date of Patent: Sep. 21, 1993

[54] DISPOSABLE FLOSS PICK AND METHOD OF MANUFACTURE

[76] Inventor: Harry S. Katz, 785 Pleasant Valley Way, West Orange, N.J. 07052

[21] Appl. No.: 837,646

[22] Filed: Feb. 14, 1992

[51] Int. Cl.⁵ .............................. A61C 15/00
[52] U.S. Cl. ................................. 132/323
[58] Field of Search ..................... 132/323, 327

[56] References Cited

U.S. PATENT DOCUMENTS

| | | | |
|---|---|---|---|
| 2,180,522 | 11/1939 | Henne | 132/323 |
| 2,217,917 | 10/1940 | Munro | 132/326 |
| 2,648,341 | 8/1953 | Moll | 132/323 |
| 2,784,722 | 3/1957 | Chamberlin et al. | 132/324 |
| 2,837,098 | 6/1958 | Sorboro | 132/324 |
| 3,918,466 | 11/1975 | Peebles, Jr. | 132/323 |
| 3,926,201 | 12/1975 | Katz | 132/323 |
| 3,974,842 | 8/1976 | Chodorow | 132/323 |
| 4,006,750 | 2/1977 | Chodorow | 132/323 |
| 4,655,233 | 4/1987 | Laughlin | 132/323 |

*Primary Examiner*—Robert P. Swiatek
*Assistant Examiner*—Nicholas D. Lucchesi
*Attorney, Agent, or Firm*—Mitchell P. Novick

[57] ABSTRACT

A disposable dental floss pick comprising a length of floss filament bonded to a plastic handle. The floss pick may be either a single plastic layer with the floss on top or a laminate comprising two plastic layers with the floss in between. Also, a method of rapidly and economically producing a dental floss pick utilizing continuous or progressive steelrule die cutting is described.

13 Claims, 2 Drawing Sheets

DISPOSABLE FLOSS PICK AND METHOD OF MANUFACTURE

BACKGROUND OF THE INVENTION

1. Field of the Invention

This invention relates to dental floss picks, and more particularly, to a low cost, plastic, disposable dental floss pick and method of manufacture.

2. Description of Prior Art

The daily use of dental floss is desirable for a number of reasons. It is a means of cleaning between the teeth and under gum margins so that bacterial or dental plaque is removed. Dental authorities consider plaque the leading cause of periodontal disease and tooth loss in adults. Also, dental floss is the best means for removal of food particles between the teeth after eating. The trapped particles are annoying, may interfere with proper speech, and when permitted to remain, may cause bad breath. The standard wood or plastic tooth picks that are usually used for this purpose have a number of shortcomings, among them the tendency to break during use, sharp edges which may cut into the gums and cause bleeding, and a leading point which is often too thick to dislodge particles from narrow spaces between teeth.

Prior art in this field discloses that existing disposable dental floss picks have generally been made by a process that injection molds plastic material around a strand of flossing material, producing a chain of floss picks; the floss picks are then separated by cutting apart the floss between consecutive floss picks. The following patent represents the state of the art: U.S. Pat. Nos. 3,926,201, granted to Harry S. Katz, the inventor of the present application. Injection molding, as specified in Katz, is an excellent method for producing this type of product, and has been used for large scale production of this type of product, but involves significant costs in mold set-up and maintenance. The present invention is an innovative and nonobvious improvement over Katz and the other prior art.

SUMMARY OF THE INVENTION

A primary object of the present invention is to provide a disposable dental floss pick which can be produced more quickly and more economically than currently available disposable dental floss picks.

Another object of this invention is to provide a method for manufacturing dental floss picks utilizing an economical steel-rule die cutting process and a quick, low-cost bonding process.

In short, the instant invention is a dental floss pick in which the floss is secured to the handle via adhesive means, such as hot melt adhesive bonding, ultraviolet curing, or ultrasonic swaging. The floss pick is produced from sheets of plastic, utilizing a progressive and continuous steel-rule die cutting process in combination with a rapid bonding process.

This is a very effective method for producing a disposable floss pick and is a significant and novel improvement over existing methods for reasons that include the following:

(1) Start-up costs and time are relatively low compared to procuring injection molding equipment and molds;

(2) This invention does not necessitate the on-going extensive maintenance and intense supervision typical of injection molding processes;

(3) The floss is secured to the floss pick using rapid and low-cost means, such as hot melt adhesive bonding, ultraviolet curing, or, ultrasonic swaging;

(4) The steel-rule die cutting process simultaneously cuts both the floss pick shape and the floss; and (5) The handle is a significant part of the materials expense. With a steel-rule die cutting process, the handle can be of a shape in which there is minimal or no waste material between consecutive floss picks cut from a long strip or sheet of plastic. Furthermore, because the material is thermoplastic, any waste from die cutting can be recycled through the extruder that is used to produce the plastic sheets. Thus, material costs are minimized.

DESCRIPTION OF PREFERRED EMBODIMENTS

Figure 1:
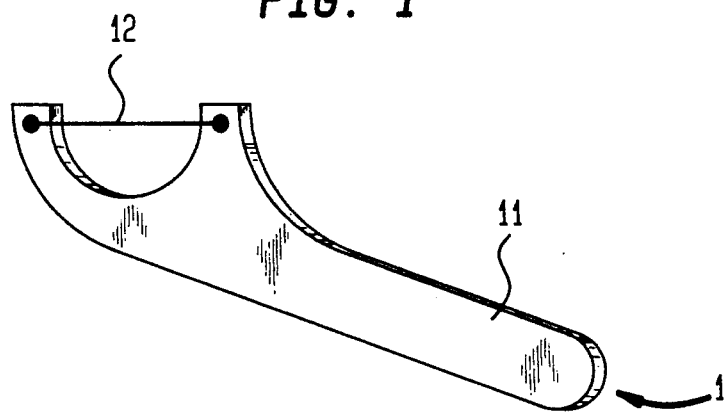
FIG. 1 is a top view of a one-layer dental floss pick.
Figure 2:
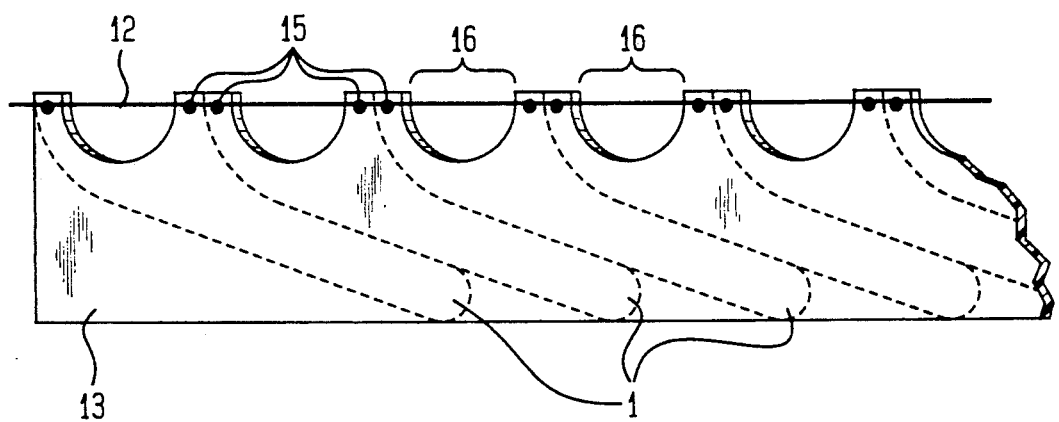
FIG. 2 is a top view of a plastic sheet, with cutouts and floss attached, from which will be cut numerous dental floss picks shown in FIG. 1.
Figure 3:
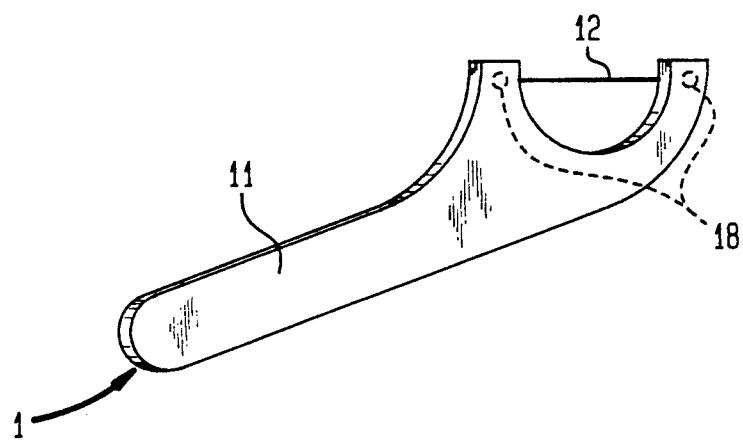
FIG. 3 is a bottom view of the dental floss pick shown in FIG. 1.
Figure 4:
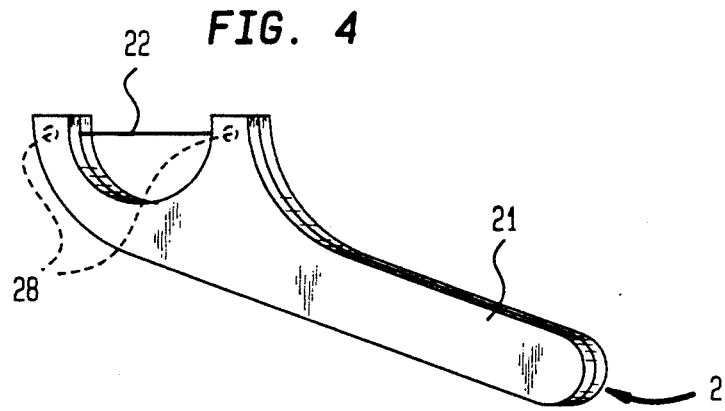
FIG. 4. is a top view of a two-layer laminate dental floss pick, in which the floss is sandwiched between two layers of plastic.
Figure 5:
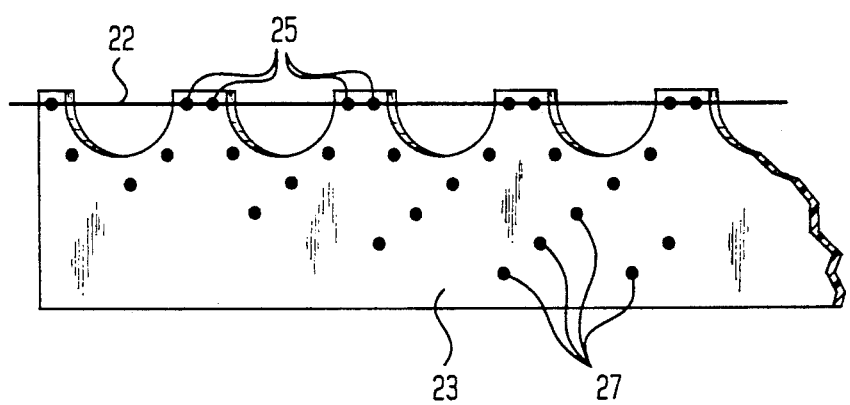
FIG. 5. is a top view of a single plastic sheet, with cutouts and floss attached, with floss during the manufacturing process of the dental floss pick shown in FIG. 4.
Figure 6:
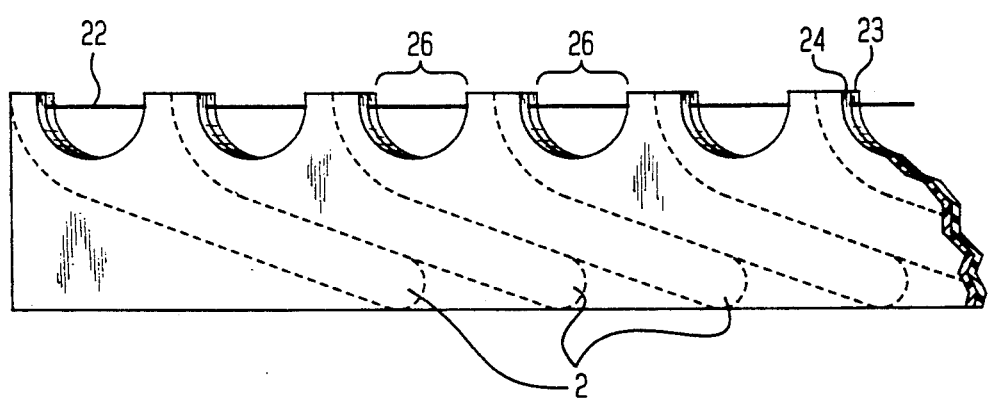
FIG. 6. is a top view of the composite laminate from which will be cut numerous dental floss picks shown in FIG. 4.
Figure 7:
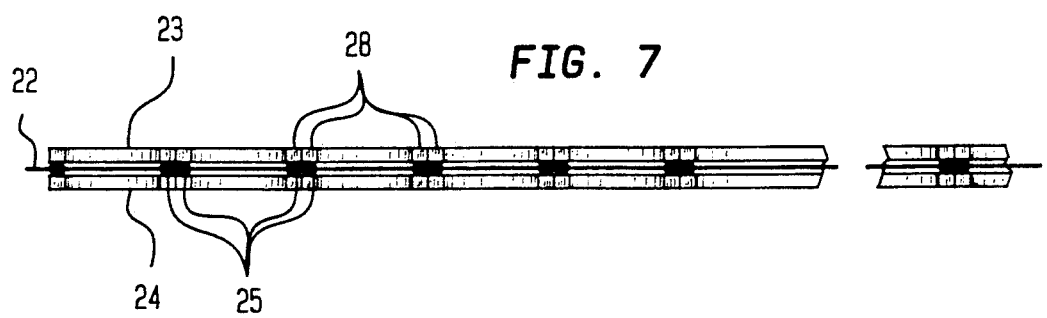
FIG. 7. is a side view of the composite laminate shown in FIG. 6.

The floss pick comprises a length of floss filament bonded to a thermoplastic. The preferred thermoplastic is one that is lightweight, semirigid, inexpensive, easy to work with, non-toxic, and non-damaging to teeth and gums. Preferably, this material is 40% talc-filled polypropylene, formed into a sheet about 0.040-inch thick and 2 inches wide. The talc gives the polypropylene added rigidity, which is desirable for a dental floss pick. Alternative materials are unfilled polypropylene, linear polyethylene, and nylon sheet. All of these plastics are thermoplastic, which is preferred over thermosetting because they are less brittle and more economical to use.

The floss filament comprises standard dental floss approved by United States Food and Drug Administration ("FDA"). Such dental floss is readily available from dental laboratory supply companies such as Johnson & Johnson.

The floss picks are prepared preferably by a steel-rule die cutting process. The preferred process uses a single "cavity" progressive steel-rule die, in which a single cut is made during each cycle. Multiple cavity dies may also be used. In this method, the plastic sheet comprises a belt of plastic, moving intermittently and continuously through an automated line. At each station along the line occurs another of the manufacturing steps.

In addition, the handles of the floss picks can be stamped or printed to include instructions, advertising slogans, or designs. This stamping or printing preferably would be done at a station along the automated manufacturing line, rather than ina separate process as required for injection-molded floss picks.

Preferably, the floss picks are shaped so consecutive floss picks have a common edge between them. Thus, there is minimal waste of material and maximum use of the plastic sheet in the manufacturing process.

One-Layer Floss Pick

In the first preferred embodiment, the disposable floss pick 1 comprises a one-layer plastic handle 11 having a cutout 16 with a length of floss 12 stretched across the cutout 16 on the top surface of the handle 11. The handle 11 is shaped to be held between the thumb and one other finger. The cutout 16 is preferably semicircular- or U-shaped.

The preferred attachment means is a drop of adhesive 15 on the handle 11 near each end of the length of floss 12. The drops of adhesive 15 are preferably a hot melt adhesive that has FDA approval. Other adhesives may be used, such as ultraviolet-curable adhesive which will be cured by exposure to an ultraviolet lamp.

Alternatively, the floss length 12 may be bonded to the handle 11 by non-adhesive means, preferably ultrasonic swaging. When the sheet 13 contains the alignment holes 18, during ultrasonic swaging, some plastic material is forced into the holes 18 which also forces a section of floss 12 around the holes to deform and partially enter the holes 18. This mechanical deformation of the floss 12 creates a "mechanical lock" between the floss 12 and the handle 11, in addition to the adhesive bond.

The preferred manufacturing process for the floss pick 1 follows:

First, using a steel-rule die, preferably a progressive or rotary type, a sheet 13 is cut to produce cutouts 16 that define the selected working length of the floss 12 in each pick 1. These cutouts 16 are preferably semicircular- or U-shaped. This cutting operation also produces small holes 18 as an aid in aligning the lengths of floss 12 and in securing the floss 12 to the handle 11. The alignment holes 18 may be omitted.

Second, lengths of floss 12 are placed across the cutouts 16. If there are alignment holes 18, the floss 12 is aligned across the holes 18. Preferably, one continuous piece of floss comprises the lengths of floss 12 for all picks 1 to be produced from the sheet 13.

Third, drops of adhesive 15 are placed on the floss 12 near each end of the length of floss 12. If there are alignment holes 18, the adhesive drops 15 are placed at the location of the holes 18.

Fourth, using another steel-rule die, preferably a progressive or rotary type, a final die cutting occurs which cuts the sheet 13 and floss into the final individual floss picks 1.

Two-Layer Laminate Floss Pick

In the second preferred embodiment, the disposable floss pick 2 comprises a two-layer laminate plastic handle 21 having a cutout 26 with a length of floss 22 stretched across the cutout 26 in between the two layers 23, 24 of the handle 21. As in the first preferred embodiment, the handle 21 is shaped to be held between the thumb and one other finger. The cutout 26 is preferably semicircular- or U-shaped.

The preferred attachment means of the length of floss 22 is a drop of adhesive 25 in the handle 21 near each end of the length of floss 22. The length of floss 22 is preferably attached to only sheet 23, but may be attached to both sheets 23, 24. The two layers 23, 24 of the handle 21 are attached preferably by drops of adhesive 27 distributed across the handle 21 in moderate density. The drops of adhesive 25, 27 are preferably a hot melt adhesive that has FDA approval. Other adhesives may be used, such as ultraviolet-curable adhesive which will be cured by exposure to an ultraviolet lamp.

Alternatively, the floss length 22 may be bonded to the handle 21 by non-adhesive means, preferably ultrasonic swaging. When a sheet 23, 24 to which the floss length 22 is being attached contains the alignment holes 28, during ultrasonic swaging, some plastic material is forced into the holes 28 which also forces a section of floss 22 around the holes to deform and partially enter the holes 28. This mechanical deformation of the floss 22 creates a "mechanical lock" between the floss 22 and the handle 21, in addition to the adhesive bond.

The preferred manufacturing process for the floss pick 2 follows:

First, using a steel-rule die, preferably a progressive or rotary type, two sheets 23, 24 are cut to produce cutouts 26 that define the selected working length of the floss 22 in each pick 2. These cutouts 26 are preferably semicircular- or U-shaped. This cutting operation also produces small holes 28 as an aid in aligning the lengths of floss 22 and in securing the floss 22 to the handle 21. The alignment holes 28 may be omitted.

Second, lengths of floss 22 are placed across the cutouts 26 in one sheet 23. If there are alignment holes 28, the floss 22 is aligned across the holes 28. Preferably, one continuous piece of floss comprises the lengths of floss 22 for all picks 2 to be produced from the sheet 23.

Third, drops of adhesive 25 are placed on the floss 22 near each end of the length of floss 22. If there are alignment holes 28, the adhesive drops 25 are placed at the location of the holes 28.

Fourth, drops of adhesive 27 are applied as small beads uniformly and in moderate density across the surface of the sheet 23 to which the length of floss 22 is attached.

Fifth, the second sheet 24, is positioned above sheet 23 and the floss so that the corresponding cutouts 26 in sheets 23, 24 are aligned, and the sheets 23, 24 are secured via the adhesive drops 27.

Sixth, using another steel-rule die, preferably a progressive or rotary type, a final die cutting occurs which cuts the sheet 23 and floss into the final individual floss picks 2.

Alternatively, this laminate may also be formed by joining sheets 23, 24 by non-adhesive means, preferably ultrasonic swaging.

Although this invention has been described with a certain degree of particularity, it is to be understood that the present disclosure has been made only by way of illustration and that numerous changes in the details of the method may be resorted to without departing from the spirit and scope of this invention.

I claim:

1. A dental floss pick comprising:
   a handle having two arms with a common end, each said arm having flat first and second surfaces and an unattached end opposite to said common end;
   dental floss filament having first and second floss ends; and
   adhesive bonding means on one of said first and second surfaces of each arm, adhesively bonding said floss filament to and against said one surface of each arm, at said first and second floss ends, so that said floss ends are not embedded within said arms nor wound about them.

2. A dental floss pick as described in claim 1, wherein said adhesive bonding means comprises hot melt adhesive.

3. A dental floss pick as described in claim 1, wherein said adhesive bonding means comprises ultraviolet-curable adhesive.

4. A dental floss pick as described in claim 1, in which each said arm has an alignment opening corresponding to each of said first and second floss ends.

5. A dental floss pick comprising;
a handle having two arms with a common end, each said arm having an unattached end opposite to said common end; said handle further comprised of a first layer and a second layer;
dental floss filament having first and second floss ends; and
adhesive bonding means, of relatively uniform thickness, between said first and second layers, said adhesive bonding means adhesively bonding said floss filament to said handle between said unattached ends of said arms and between said first and second layers, at said first and second floss ends, and also adhesively bonding together said first and second layers, so that said floss ends when so bonded are not subjected to nontrivial bending stresses.

6. A dental floss pick as described in claim 5, wherein said adhesive bonding means comprises hot melt adhesive.

7. A dental floss pick as described in claim 5, wherein said adhesive bonding means comprises ultraviolet-curable adhesive.

8. A dental floss pick as described in claim 5, in which each said arm has an alignment opening corresponding to each of said first and second floss ends.

9. A method of producing a dental floss pick comprising a handle having two arms with a common end, each said arm also having flat first and second surfaces and an unattached end opposite to said common end, dental floss filament strung across said arms along a top surface of said handle, and adhesive bonding means on one of said first and second surfaces of each arm, adhesively bonding said floss filament to and against said one surface of each arm at said unattached ends, so that said floss ends are not embedded within said arms nor wound about them, said method comprises the steps of:
  (a) stretching an elongated dental floss filament across said one surface of each arm along said unattached ends;
  (b) providing adhesive bonding means to said unattached ends on said one surface of each arm in volume sufficient to surround a portion of said elongated floss filament stretching across said one surface of each arm, said adhesive bonding means being susceptible to adhesive bonding and rapid setting; and
  (c) rapidly setting said adhesive bonding means, thereby adhesively bonding said dental floss filament to and against said one surface of each arm.

10. A method as described in claim 9, wherein said adhesive bonding means comprises ultraviolet-curable adhesive and said setting step comprises an ultraviolet energy curing process.

11. A method as described in claim 9, wherein said rapid setting material comprises hot melt plastic adhesive and said setting step comprises a cooling process.

12. A method of producing a plurality of dental floss picks from a strip of plastic, said method comprising:
  (a) steel-rule die cutting of a plurality of floss openings in said strip;
  (b) stretching an elongated floss filament across said floss openings;
  (c) securing said floss filament to said strip, producing a plastic-floss composite;
  (d) steel-rule die cutting of said dental floss picks from said plastic-floss composite.

13. A method of producing a plurality of laminate dental floss picks from first and second strips of plastic, said method comprising:
  (a) steel-rule die cutting of a plurality of floss openings in said first and second strips;
  (b) stretching an elongated floss filament across said floss openings in said first strip;
  (c) placing said second strip on top of said first strip and said floss filament, such that said floss openings in said second strip are aligned with corresponding said floss openings in said first strip;
  (d) securing to each other said first and second strips, with said floss filament in between said first and second strips, producing a plastic-floss laminate;
  (e) steel-rule die cutting of said dental floss picks from said plastic-floss laminate.

* * * * *